United States Patent [19]

Takashima

[11] 4,279,909

[45] Jul. 21, 1981

[54] ANTIALLERGIC METHOD

[75] Inventor: Toshiyuki Takashima, Nagaoka, Japan

[73] Assignee: Fujisawa Pharmaceutical Co., Ltd., Osaka, Japan

[21] Appl. No.: 121,039

[22] Filed: Feb. 13, 1980

[51] Int. Cl.³ .................................... A61K 31/495
[52] U.S. Cl. .................................... 424/250
[58] Field of Search .................. 544/368; 424/250

[56] References Cited

U.S. PATENT DOCUMENTS

| | | | |
|---|---|---|---|
| 3,661,921 | 5/1972 | Umio | 544/368 |
| 3,755,329 | 8/1973 | Umio | 544/368 |
| 4,131,681 | 12/1978 | Takashima | 424/267 |

OTHER PUBLICATIONS

IX International Congress of Allergy, Oct. 28, 1976, Buenos Aires.
Fifth International Congress on Pharmacology, Jul. 23–28, 1972, San Francisco.

*Primary Examiner*—Leonard Schenkman
*Attorney, Agent, or Firm*—Oblon, Fisher, Spivak, McClelland & Maier

[57] ABSTRACT

The invention relates to certain 3-substituted-carbonyl (lower) alkyl-2-benzothiazolinone compounds possessing strong antiallergic properties, and to prophylactic and therapeutic treatments by administration of said compounds.

5 Claims, No Drawings

ANTIALLERGIC METHOD

This invention relates to the discovery that certain 3-substituted-carbonyl(lower)alkyl-2-benzothiazolinone compounds and pharmaceutically acceptable salt thereof possess strong antiallergic properties. These compounds are represented by the formula:

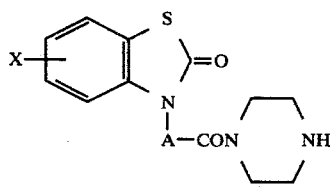

wherein A is lower alkylene and X is halogen, in which the lower alkylene group for the symbol A is exemplified with methylene, ethylene, trimethylene, propylene, tetramethylene, ethylethylene, etc., and it preferably means one having 1 to 3 carbon atom(s) and more preferably one having 1 to 2 carbon atom(s) and most preferably methylene, and halogen atom for the symbol X includes chlorine, bromine, iodine and fluorine and preferably means chlorine and bromine and most preferably chlorine, where there may be optional the positions substituted of the symbol X on the benzothiazolinone ring, preferably the 5th position.

This invention relates, more particularly, to use of the compound (I) or pharmaceutically acceptable salt thereof as antiallergic agent for prophylaxis and therapy to mammals, to method for treating allergic diseases by administering the compound (I) or pharmaceutically acceptable salt thereof per se or in a pharmaceutical form thereof and also to pharmaceutical composition useful as antiallergic agents which comprises one or more compound(s) selected from the group represented by the compound (I) and pharmaceutically acceptable salt thereof.

Suitable pharmaceutically acceptable salt of the compound (I) may include an acid addition salt such as an inorganic acid salt (e.g. hydrochloride, hydrobromide, etc.) or an organic acid salt (e.g. acetate, maleate, etc.).

The compound (I) is known to the public by the disclosure of U.S. Pat. No. 3,755,327.

It is understood from the disclosure of said USP that the compound (I) possesses inhibitory activity of central nervous system, antiinflammatory activity and antiarrhythmic activity.

It was discovered by the inventor that tiaramide hydrochloride, i.e. 3-[4-(2-hydroxyethyl)-1-piperazinyl-carbonylmethyl]-5-chloro-2-benzothiazolinone hydrochloride, possesses antiallergic activity, which was presented by him at the IX International Congress of Allergy on Oct. 28, 1976 at Buenos Aires, Argentina.

After that, it was also discovered by the inventor that 3-(hydroxypiperidino)carbonylmethyl-5-chloro-2-benzothiazolinone possesses antiallergic activity, which is known to the public by the disclosure of U.S. Pat. No. 4,131,681.

The inventor of this invention has found out that the compound (I) and pharmaceutically acceptable salt thereof is much more potent in antiallergic activity than tiaramide hydrochloride and 3-(hydroxypiperidino)carbonylmethyl-5-chloro-2-benzothiazolinone.

Hitherto antiallergic drugs have been put on the market, and some of them are now practically employed for prophylactic and therapeutical purposes. However, the drugs are well known and although practically accepted still have undesirable effects and are thus inconvenient for practical use. For example, synthesized derivatives of adrenal cortical steroid hormone show typical adverse reactions which are well known to those in the art, such as mental disorders, peptic ulcer, induction and aggravation of infections (especially tuberculosis, mycosis and septicemia), adrenal cortical insufficiency, diabetes and osteoporosis, and Isoproterenol, an adrenergic β-receptor stimulant, shows an unfavorable activity on cardiovascular system, e.g. tachycardia, at the dosage administered for treatment of allergic symptoms and, in the long-term treatment with this drug, may cause, suffocation because it causes an increase in the viscosity of the sputum and thus makes it more difficult for patients to cough up the accumulated sputum from the respiratory tract. Due to these undesirable properties, the above mentioned drugs have to be used under severe control of doctors or professionals.

Another antiallergic agent, disodium cromogycate, which is accepted as a desirable antiallergic drug, is not so effective when used orally, and is usually administered in the forms of injection and inhalation. The impossibility of oral administration causes inconvenience and uneasiness in practical use, especially for infants. Also, this drug is very useful for prophylactic purpose but not so useful for the so-called symptomatic treatment because it does not exert the inhibitory effect on allergic symptoms.

The inventor of this invention has further studied and found that the compound (I) and pharmaceutically acceptable salt thereof can produce immediate effect and therefore it can be employed orally or parenterally for therapeutical use as well as prophylactic use, as an antiallergic agent having less side effects in a various pharmaceutical forms.

Accordingly, an object of this invention is to provide a method for utilizing the antiallergic activity of the compound (I) and pharmaceutically acceptable salt thereof prophylactically of therapeutically for inhibiting or relieving symptoms associated with allergic diseases, especially bronchoconstruction in asthma.

Another object of this invention it to provide a method for treating allergic diseases to prevent or relieve allergic symptoms.

Further object of this invention is to present a pharmaceutical composition useful as antiallergic agent in a pharmaceutical form for oral or parenteral use.

The following pharmacological data are given to illustrate desirable and superior properties of the representative compound of the compound (I), i.e. 3-(1-piperazinyl)carbonylmethyl-5-chloro-2-benzothiazolinone (referred to Compound A hereinafter) in comparison with the known antiallergic drugs and compound, i.e. tiaramide hydrochloride (referred to Compound B hereinafter), 3-(4-hydroxypiperidino)carbonylmethyl-5-chloro-2-benzothiazolinone (referred to Compound C hereinafter) and disodium chromoglycate (referred to Compound D).

EXPERIMENT (1) Preparation of antiserum (a) Rat reaginic antiserum against egg albumin One mg of egg albumin emulsified in 0.5 ml of B. pertussisdiphtheria mixed vaccine (Tanabe Seiyaku Company Ltd.) and 0.5 ml of Freund's incomplete adjuvant (Difco) was used as the antigen. The emulsion was given subcutaneously in a single dose of 1 ml divided equally (0.25 ml) to the four foot pads of male Sprague-Dawley JCL strain rats aged 6 weeks, each weighing 170–220 g. Blood samples were collected from the femoral artery 12 days after injection, and centrifuged at 3000 r.p.m. at 4° C. for 15 minutes. The antisera thus obtained were stored at −20° C.

(b) Rat hyperimmune antiserum against egg albumin

Male Sprague-Dawley JCL strain rats were injected in the four foot pads with 10 mg of egg albumin emulsified in 0.5 ml of saline and 0.5 ml of Freund's complete adjuvant in divided portions. Seven days later, the animals were injected intramuscularly at three sites on a shaved area of their backs with a total of 5 mg of egg albumin emulsified in 0.5 ml of saline and 0.5 ml of Freund's complete adjuvant. On days 28 to 30, the animals were injected intracutaneously at two sites on the back with 0.2 mg of egg albumin in 0.2 ml of saline. The antiserum was obtained 7 days after the last injection and stored at −20° C.

(c) Guinea-pig antiserum against egg albumin

Five mg of egg albumin emulsified in 0.5 ml of physiological saline and 0.5 ml of Freund's incomplete adjuvant was used as the antigen.

The emulsion was given subcutaneously in a single dose of 1 ml divided equally (0.25 ml) to the four foot pads of male Hartly strain guinea pigs, each weighing 250 to 300 g. Starting two weeks after dosing with the aforementioned emulsion 0.1% egg albumin emulsified in physiological saline was given subcutaneously in equally divided (0.1 ml) doses of 0.4 ml once a week for 4 weeks to four sites on the backs of the test animals. Blood samples were collected from the carotid artery one week after the last injection, and centrifuged at 3000 r.p.m. at room temperature for 15 minutes. The antisera thus obtained were stored at −20° C.

(2) Antagonism to passive cutaneous anaphylaxis (P.C.A.) in rat sensitized with homologous reaginic antiserum Ten male Sprague-Dawley-JCL strain rats, weighing 290–310 g were used for each dose. The rat reaginic antiserum against egg albumin was used at a dilution 1:4. The animals were sensitized with 0.1 ml of the antiserum injected intracutaneously on the depilated backs of the rats. Fortyeight hours after the injection of the antiserum, 1 ml of mixture of egg albumin 5 mg and Evans' blue 5 ml in physiological saline 1 ml was injected intravenously. Thirty minutes after the injection of the antigen, animals were sacrificed and the skin was removed. To each sensitized area of the skin was added 10 ml of 4:1 mixture of acetone and 2% solution of RBS-25 (Marumoto Industrial Co., Ltd.) to extract the dye and the mixture was allowed to stand for 16 hours, during of which the mixture was twice shaken for 30 minutes at 5th hour and 16th hour. It was further centrifuged at 2000 r.p.m. for 15 minutes and the quantity of the dye in the supernatant solution was determined by colorimetry at 620 m$\mu$. Test compound was given orally 2 hours and intravenously 5 minutes before administration of the antigen. The inhibitory effect of test compound was determined from the dye amounts measured in comparison with the control group and the treated group and the ED$_{50}$ value was calculated according to Litchfield-Wilcoxon method.

RESULTS

The ED$_{50}$ value of Compound A: 50 mg/kg (3) Passive cutaneous anaphylaxis (P.C.A.) in rats sensitized with homologous hyperimmune antiserum P.C.A. reaction was performed in male Sprague-Dawley JCL strain rats passively sensitized with homologous hyperimmune antiserum against egg albumin. That is, 0.1 ml of the antiserum was injected into the skin on the back of rats, and 4 hours later 1 ml of mixture of egg albumin 5 mg and Evans' blue 5 mg was injected intravenously. One hour later, the animals were killed and the skin was removed. Evans' blue was then extracted from the sensitized spot with 10 ml of 4:1 mixture of aceton and 2% solution of RBS-25. The quantity of Evans' blue was determined by colorimetry at 620 m$\mu$. The drug was given intravenously 30 seconds before dosing with antigen.

TABLE 1

| Inhibitory effect of P.C.A. reaction in rats sensitized with rat hyperimmune antiserum | | | | |
|---|---|---|---|---|
| | Test Compound | | | |
| | Compound A | Compound B | Compound C | Compound D |
| ED$_{50}$(mg/kg) | 9 | 28 | 32 | 105 |

(4) Anaphylactic bronchoconstriction in guinea-pigs sensitized with homologous antiserum Male Hartly strain guinea-pigs were sensitized with an intravenous injection of 1 ml of homologous antiserum against egg albumin. And 48 hours later, the animals were immobilized with an intraperitoneal dose of 100 mg/kg of gallamine. The trachea was cannulated for artificial respiration which was performed with a miniature respiratory pump (3 ml/stroke, 60 strokes/minute). The side-arm of the canula was connected to a strain gauge to measure the pressure of superfluous air through the side-arm of the canula. One mg/kg of egg albumin was injected intravenously to produce anaphylactic bronchoconstriction to give a rise of pressure. The drug was injected intravenously 30 seconds before dosing with the antigen.

RESULTS

The ED$_{50}$ value of Compound A: 56 mg/kg (5) Antagonistic effect on histamine in vitro Isolated guinea-pig ileum was set up in an organ bath containing Tyrode solution at 27° C., and aerated with 95% $O_2$ and 5% $CO_2$. The ileum was connected to a strain gauge transducer and the contractions were recorded isometrically. A constriction in strength of 2.0 to 5.0. g was obtained by histamine ($1.0 \times 10^{-7}$ g/ml).

TABLE 2

| Percentage inhibition of histamin ($1.0 \times 10^{-7}$ g/ml) | | | |
|---|---|---|---|
| Concentration | Test Compound | | |
| (g/ml) | Compound A | Compound B | Compound D |
| $1.0 \times 10^{-5}$ | 14 | 6 | 2 |
| $4.0 \times 10^{-5}$ | 48 | 18 | 4 |
| $8.0 \times 10^{-5}$ | 59 | 24 | — |
| $1.6 \times 10^{-4}$ | 82 | 49 | 1 |

(6) Acute toxicity in mouse and rat

Each ten male and female ICR-JCL strain mice and Sprague-Dawley-JCL strain rats were used for each dose.

Test compound was given to animals in a form of suspension in 0.5% methyl cellose orally. After administration, the incidence of the death was recorded for successive seven days. $LD_{50}$ values were calculated by the method of Lichfield-Wilcoxon method.

RESULTS

The $LD_{50}$ value of Compound A:
219 mg/kg (Female mouse);
734 mg/kg (Female rat)

It is apparent from the above data that the compound (I) shows excellent properties in antiallergic action.

In practice of the method of this invention, effective amount of the compound (I) itself or pharmaceutical compositions thereof is administered to mammals including human beings via any of the conventional and acceptable methods known in the art.

The active ingredient of this invention can be accepted either singly or in combination with another compound or compounds selected from the group represented by the Compound (I) or other pharmaceutical agents such as analgesic agents, antibiotics, hormonal agents and the like.

The antiallergic active ingredient compound (I) can be administered via oral or parenteral route in various pharmaceutical forms such as capsules, microcapsules, tablets, granules, powders, troches, pills, ointments, suppositories, injectable solutions, syrups, aerosols, inhalations, etc.

The antiallergic effectiveness in prophylaxis and therapy of the compound (I) is demonstrated, when administered by oral or rectal route or injection or inhalation, at varying dose ranges within the effective amount which starts about 0.1 mg/kg/day and raised upwards to a level below manifestation of undesirable effects, generally 200 mg/kg/day.

In topical applications such as ointment or inhalation, it is necessary to apply the active ingredient, itself or in pharmaceutical composition, to be maintained in a sufficient concentration to a designated topical part.

In prophylactic and therapeutical use, the active ingredient is employed for human beings in the following doses:

| Administration Route | Dose (mg/kg/day) |
|---|---|
| oral | 5 to 100 |
| rectal | 25 to 200 |
| Injection (i.v.) | 0.25 to 25 |
| (s.c. and i.m.) | 0.30 to 30 |
| inhalation | 1 to 10 | and ointment is usually administered to skin in a ratio of 100 to 2000 mg per the whole surface of back of human beings for one time application.

The administration dosages are varied considerably taking into account several conditions such as the age of the subject, the degree of prophylactic and therapeutic effect desired, etc.

In practical use, suitable amount of the active ingredient itself or pharmaceutical composition thereof is usually taken one to five time(s) a day. Among conventionally and conveniently employed forms of pharmaceutical compositions, for example, preferred dosage unit of tablets is 50, 100 or 200 mg; ampoule for injectable application in intravenous route 12.5 or 25 mg and in subcutaneous or intramuscle route 15 or 30 mg and suppository 500 mg.

The pharmaceutical compositions of this invention can contain various organic or inorganic carrier materials, which are conventionally used for pharmaceutical purpose such as excipient (e.g. sucrose, starch, mannit, sorbit, lactose, glucose, cellulose, talc, calcium phosphate, calcium carbonate, etc.), binding agent (cellulose, methyl cellulose, hydroxypropyl cellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc. ], aqueous diluting agent (e.g. water), base wax (e.g. cacao butter, polyethyleneglycol, witepsol, white petrolatum, etc.)

The following Examples are given to illustrate this invention, but said invention is not limited thereto.

EXAMPLE 1

Formula for granules or small grains
Compound A: 500 (g)
Sucrose: 9250
Hydroxypropyl cellulose: 200
Starch: 50

The above ingredients are blended and granulated or grained, in a conventional manner, into granules or small grains.

EXAMPLE 2

Formula for capsules
Compound A: 500 (g)
Starch: 1987
Magnesium stearate: 13

The above ingredients are blended and filled in hard-gelatin-capsules, in a conventional manner, to give 10,000 capsules, each of which contains 50 mg of an active ingredient, Compound A.

EXAMPLE 3

Formula for dry-syrup
Compound A: 500 (g)
Sucrose: 9250
Citric acid: 20
Hydroxypropyl cellulose: 200
Sodium benzoate: 50

The above ingredients are blended in a conventional manner to make dry-syrup.

EXAMPLE 4

Formula for tablets
Compound A: 20000 (g)
Lactose: 10400
Starch: 3600

Ethyl Cellulose: 1800
Magnesium Stearate: 200

The above ingredients are blended and compressed, in a conventional manner, into 100,000 tablets weighing 360 mg, each of which contains 200 mg of an active ingredient, Compound A. Thus obtained tablets are, when desired, coated with sugar-coating, film-coating or enteric coating.

EXAMPLE 5

Formula for tablets
   Compound A: 5000 (g)
   Lactose: 4200
   Starch: 1100
   Ethyl cellulose: 600
   Magnesium stearate: 100

The above ingredients are blended and compressed, in a conventional manner, into 100,000 tablets weighing 110 mg, each of which contains 50 mg of an active ingredient, Compound A. Thus obtained tablets are, when desired, coated with sugar-coating, film-coating or enteric coating.

EXAMPLE 6

Formula for injectable suspension
   Compound A: 2500 (g)
   Methyl cellulose: 50
   Polyvinylpyrrolidone: 5
   Methyl p-oxybenzoate: 10
   Polysorbate 80: 10
   Lidocaine hydrochloride: 50

The above ingredients are suspended in distilled water for injection to give injectable solution 10 l and divided to 100 ampoules, in a conventional manner, each of which contains 25% of an active ingredient, Compound A.

EXAMPLE 7

Formula for suppositories
   Compound A: 500 (g)
   Witeposl H12: 1700

The above ingredients are blended and compressed, in a conventional manner, into 1,000 suppositories weighing 2,200 mg, each of which contains 500 mg of an active ingredient, Compound A,

EXAMPLE 8

Formula for suppositories
   Compound A: 500 (g)
   Polyethyleneglycol 1500: 1275
   Polyethyleneglycol 4000: 425

The above ingredients are blended and compressed, in a conventional manner, into 1,000 suppositories weighing 2,200 mg, each of which contains 500 mg of an active ingredient, Compound A.

EXAMPLE 9

Formula for ointments
   Compound A: 500 (g)
   White petrolatum: 9025
   Sorbitan trioleate: 475

The above ingredients are blended and kneaded into ointment.

EXAMPLE 10

Formula for ointments
   Compound A: 1000 (g)
   White petrolatum: 8550
   Sorbitan trioleate: 450

The above ingredients are blended and kneaded into ointment.

EXAMPLE 11

Formula for ointments
   Compound A: 5000 (g)
   White petrolatum: 40000
   Sorbitan sesquioleate: 5000
   Cetanol: 18000
   Lauromacrogol: 500
   Butyl p-oxybenzoate: 100

The above ingredients are blended with distilled water and kneaded into ointment.

EXAMPLE 12

Formula for Capsules for inhalation
   Compound A: 250 (g)
   Lactic acid: 250

The above ingredients are blended and filled in 10,000 capsules of size No. 2 in a conventional manner, each of which contains 25 mg of an active ingredient, Compound A.

What we claim is:

1. A method for treating allergic diseases in mammals which comprises administering an antiallergic amount of a compound of the formula:

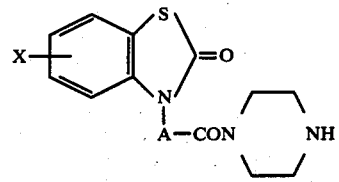

wherein A is lower alkylene and X is halogen, or a phamaceutically acceptable salt thereof, to said mammals.

2. The method of claim 1, wherein the compound is 3-(1-piperazinyl)carbonylmethyl-5-chloro-2-benzothiazolinone.

3. The method of claim 1, wherein said compound is administered in the form of a pharmaceutical composition.

4. The method of claim 1, wherein said compound is administered in the form of a shaped medicament.

5. The method of claim 1, wherein said compound with a pharmaceutically acceptable excipient is administered in the form of granules, capsules, dry-syrups, tablets, injectable suspensions, suppositories, drugs for inhalation, ointments, pills, powders, or aerosols.

* * * * *